US012802822B2

(12) United States Patent
Singh et al.

(10) Patent No.: US 12,802,822 B2
(45) Date of Patent: Nov. 17, 2026

(54) CONNECTED SMART FACE MASK WITH INTELLIGENT TRACKING

(71) Applicant: Accenture Global Solutions Limited, Dublin (IE)

(72) Inventors: Prateek Singh, Bengaluru (IN); Sudipta Mukhopadhyaya, Bangalore (IN); Mukunda Ram Bhuyan, Bangalore (IN); Bibin George, Bangalore (IN)

(73) Assignee: ACCENTURE GLOBAL SOLUTIONS LIMITED, Dublin (IE)

(*) Notice: Subject to any disclaimer, the term of this patent is extended or adjusted under 35 U.S.C. 154(b) by 829 days.

(21) Appl. No.: 18/183,784

(22) Filed: Mar. 14, 2023

(65) Prior Publication Data

US 2023/0352182 A1 Nov. 2, 2023

(30) Foreign Application Priority Data

May 2, 2022 (IN) ............................. 202241025553

(51) Int. Cl.
*G16H 50/30* (2018.01)
*A62B 9/00* (2006.01)
(Continued)

(52) U.S. Cl.
CPC ............. *G16H 50/30* (2018.01); *A62B 9/006* (2013.01); *A62B 18/025* (2013.01); *A62B 23/02* (2013.01)

(58) Field of Classification Search
CPC ........ G16H 50/30; G16H 50/20; G16H 40/63; G16H 40/67; A62B 9/006;
(Continued)

(56) References Cited

U.S. PATENT DOCUMENTS 10,561,863 B1 * 2/2020 Dashevsky .............. A62B 7/14
2017/0028231 A1 * 2/2017 Zhao ...................... A62B 9/006
(Continued)

FOREIGN PATENT DOCUMENTS

CN 111263298 A 6/2020
CN 113390688 A * 9/2021 ............ G01S 19/42
(Continued)

OTHER PUBLICATIONS

CN-113390688-A description (Year: 2021).*
(Continued)

*Primary Examiner* — Bradley H Philips
*Assistant Examiner* — Kira B Daher
(74) *Attorney, Agent, or Firm* — Mannava & Kang, P.C.

(57) ABSTRACT

In some implementations, a device may receive sensor data from an electronics module associated with a face mask. The device may process a first set of measurements included in the sensor data to determine a user mask wearing pattern that indicates whether a user is wearing the face mask in compliance with guidelines related to reducing a risk of the user spreading a respiratory illness or a risk of the user contracting a respiratory illness. The device may process a second set of measurements included in the sensor data to determine a user breathing pattern that indicates whether the user is at risk of having a medical condition or at risk of experiencing respiratory fatigue. The device may generate one or more outputs that include information related to one or more of the user mask wearing pattern or the user breathing pattern.

9 Claims, 10 Drawing Sheets

(51) Int. Cl.
*A62B 18/02* (2006.01)
*A62B 23/02* (2006.01)

(58) Field of Classification Search
CPC ........ A62B 23/00–06; A62B 18/00–10; A41D 13/11–1192; A61M 16/0605–0655
See application file for complete search history.

(56) References Cited

U.S. PATENT DOCUMENTS

| | | | | |
|---|---|---|---|---|
| 2017/0367426 | A1* | 12/2017 | Egeland | A42B 3/0433 |
| 2019/0275359 | A1* | 9/2019 | Shen | A62B 18/08 |
| 2021/0202067 | A1* | 7/2021 | Williams | H04L 67/535 |
| 2022/0059231 | A1* | 2/2022 | Saleh | G16H 40/67 |

FOREIGN PATENT DOCUMENTS

| | | | | | |
|---|---|---|---|---|---|
| FR | 3114958 | A1 | | 4/2022 | |
| GB | 2525643 | A | * | 11/2015 | A61B 5/097 |
| KR | 20210013987 | A | | 2/2021 | |
| KR | 20220048239 | A | | 4/2022 | |
| WO | WO-2017135945 | A1 | * | 8/2017 | A62B 23/02 |
| WO | 2022020957 | A1 | | 2/2022 | |

OTHER PUBLICATIONS

Extended European Search Report for Application No. EP231690991, mailed on Sep. 19, 2023, 9 pages.
Communication pursuant to Art. 94(3) EPC, mailed on Jul. 15, 2025, 5 pages.

* cited by examiner

CONNECTED SMART FACE MASK WITH INTELLIGENT TRACKING

CROSS REFERENCE TO RELATED APPLICATION

This application claims priority to Indian Patent Application No. 202241025553, filed on May 2, 2022, and entitled "CONNECTED SMART FACE MASK WITH INTELLIGENT TRACKING," the content of which is incorporated by reference herein in its entirety.

BACKGROUND

Face masks (or face coverings), such as N95 filtering facepiece respirators, surgical masks, cloth masks, or the like, may be employed as a public and/or personal health control measure against the spread of respiratory illnesses. In community and healthcare settings, face masks are generally used as source control to limit airborne transmission of pathogens and other aerosolized contaminants and/or as personal protection equipment (PPE) to prevent the wearer from being infected (e.g., by providing a mechanical barrier to block respiratory secretions that may be produced through speaking, coughing, sneezing, or singing). Accordingly, because a properly worn face mask can limit the extent to which infected individuals spread respiratory droplets and aerosols, in addition to helping to protect healthy individuals from becoming infected, masking has proven to be an effective measure to reduce transmissions of respiratory illnesses.

SUMMARY

In some implementations, a method includes receiving, by a device via a wireless link, sensor data from an electronics module associated with a face mask; processing, by the device, a first set of measurements included in the sensor data received from the electronics module to determine a user mask wearing pattern, wherein the user mask wearing pattern indicates whether a user is wearing the face mask in compliance with one or more guidelines related to reducing a risk of the user spreading a respiratory illness or a risk of the user contracting a respiratory illness; processing, by the device, a second set of measurements included in the sensor data received from the electronics module to determine a user breathing pattern, wherein the user breathing pattern indicates whether the user is at risk of having a medical condition or at risk of experiencing respiratory fatigue; and generating, by the device, one or more outputs that include information related to one or more of the user mask wearing pattern or the user breathing pattern.

In some implementations, a device includes one or more memories, and one or more processors, coupled to the one or more memories, configured to obtain sensor data that includes a first set of measurements related to a user mask wearing pattern and a second set of measurements related to a user breathing pattern, and transmit the sensor data to a user device via a wireless link.

In some implementations, a face mask includes an electronics module, wherein the electronics module includes: one or more sensors configured to obtain sensor data that includes measurements related to one or more of a state of the face mask or a user wearing the face mask; a microcontroller unit configured to process the sensor data; and a wireless communication device configured to transmit and receive information related to the sensor data over a wireless link; and a mask body that includes an interface to receive the electronics module.

DETAILED DESCRIPTION

Figure 1A:
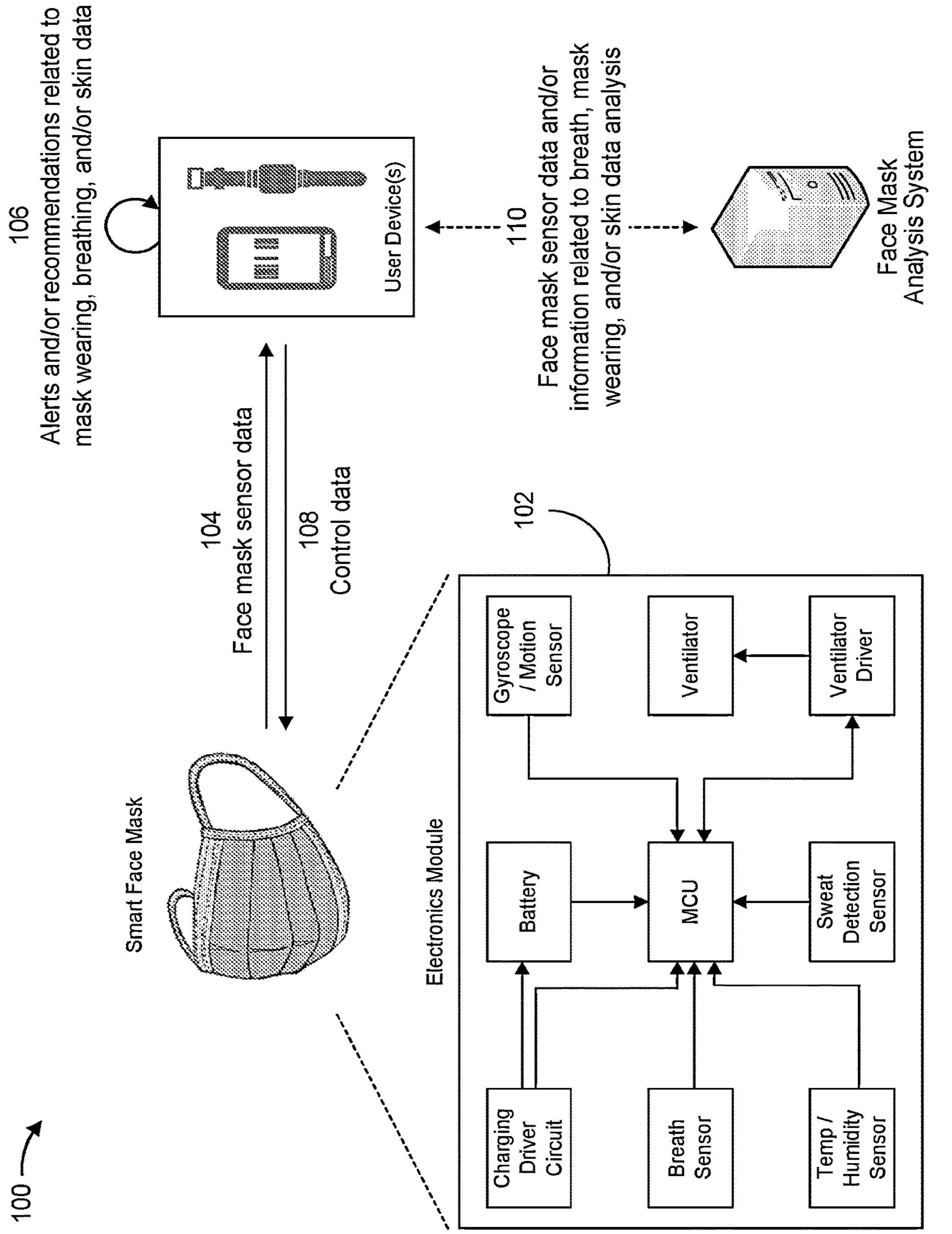
FIGS. 1A-1D are diagrams of one or more example implementations associated with a connected smart face mask with intelligent tracking.

The following detailed description of example implementations refers to the accompanying drawings. The same reference numbers in different drawings may identify the same or similar elements.

Face masks are generally designed to provide a mechanical barrier that interferes with direct airflow into and out of respiratory orifices, specifically the nose and the mouth of the wearer. As a result, face masks may help to reduce airborne transmission of virus particles, pathogens, and/or other aerosolized contaminants between the wearer and others in the vicinity of the wearer via respiratory droplets that are ejected from the nose and/or mouth when breathing, sneezing, coughing, talking, and/or singing. Although face masks tend to vary in effectiveness, with masks that satisfy the N95 and KN95 standards outperforming surgical masks (e.g., due to a better fit and a design that protects against finer airborne particles), even cloth masks with variable fabric types and mask fits can offer wearers significant protection from particles carrying airborne diseases and/or help to prevent the wearer from inhaling airborne irritants such as pollen during allergy seasons or dust particles caused by pollution.

In any case, in order to maximize effectiveness, a face mask needs to be worn correctly. For example, to reduce a risk of the wearer spreading or contracting a respiratory illness, mask wearing guidelines generally specify that a properly worn mask should fully cover the nose and the mouth of the wearer. However, common issues include people wearing masks pulled down below their nose or having a loose fit between the mask edges and the face of the wearer. In many cases, the wearer may be unaware that their nose and/or mouth is not fully covered, or the wearer may intentionally pull the mask down under the nose or remove the mask entirely (e.g., due to discomfort from excessive mask wearing or a general reluctance or unwillingness to wear the face mask, among other examples), which may reduce the public and personal protection otherwise offered by a properly fitted face mask. However, because existing face masks are designed as simple passive devices (e.g., typically made only from textiles or other material), existing face masks have no intrinsic capability to provide feedback to the wearer regarding whether the face mask is being worn correctly. Furthermore, and for similar reasons, existing face masks are unable to provide feedback regarding whether the user is breathing in a way that suggests a potential risk for having a respiratory illness or suffering from respiratory fatigue (e.g., caused by excessive mask wearing) and/or whether the wearer is at risk of developing or worsening a skin condition (e.g., caused by sweating or moisture under the face mask).

Some implementations described herein relate to a connected smart face mask that includes an electronics module to monitor and provide alerts and/or feedback related to a user mask wearing pattern, a user breathing pattern, and/or a potential skin condition of the user. For example, in some implementations, the connected smart face mask may include a mask body with an interface to receive the electronics module, which may include a microcontroller unit and various sensors configured to monitor a state associated with one or more parameters related to the user mask wearing pattern, the user breathing pattern, and/or the potential skin condition. For example, in some implementations, the sensors included in the electronics module may include a gyroscope or motion sensor to obtain parameters related to a six-axis position of the face mask relative to a face of the wearer, a breath analysis sensor to obtain parameters related to the breathing pattern of the wearer, and/or one or more environmental sensors to monitor temperature and/or moisture that may impact the comfort and/or skin irritation of the wearer. In some implementations, the electronics module may include a ventilator (e.g., a fan) that can be turned on or off as needed to provide active ventilation support (e.g., based on the user breathing pattern and/or skin condition detected from the sensor data).

Furthermore, in some implementations, the electronics module may include a communication device (e.g., a Bluetooth transceiver) that can be used to transmit the sensor data to a user device, such as a smartphone or a smartwatch, that may execute an application to determine the user mask wearing pattern, the user breathing pattern, and/or the potential skin condition of the wearer. Accordingly, the user device may generate one or more outputs (e.g., alerts, recommendations, visualizations, or the like) to provide feedback related to the user mask wearing pattern, the user breathing pattern, and/or the potential skin condition of the user. Furthermore, in some implementations, the user device may communicate with a face mask analytics system (e.g., a server in a cloud environment) to invoke more computationally intensive processing and/or enable derivation of metrics or analytics across a population of users (e.g., to enable contact tracing and/or identify patterns in sensor data that are associated with compliance or non-compliance with masking guidelines, respiratory illnesses or respiratory fatigue, or skin conditions caused by mask wearing. In this way, the connected smart face mask may provide a capability to monitor the user mask wearing pattern to ensure compliance with appropriate guidelines to reduce the risk of the wearer spreading and/or contracting a respiratory illness, analyze the user breathing pattern to detect indicators of respiratory illness or respiratory fatigue, or analyze environmental conditions under the mask to detect indicators of potential skin conditions, among other examples.

FIGS. 1A-1D are diagrams of one or more example implementations 100 associated with a connected smart face mask with intelligent tracking. As shown in FIGS. 1A-1D, example implementation 100 includes a smart face mask, a user device, and a face mask analytics system, which are described in more detail below in connection with FIGS. 2A-2C, FIG. 3, and FIG. 4.

As shown in FIG. 1A, and by reference number 102, the smart face mask may include an electronics module that includes various components to enable monitoring, tracking, feedback, and/or control to improve compliance with mask wearing guidelines that are designed to prevent the wearer from spreading and/or contracting a respiratory illness, to detect potential respiratory illnesses and/or respiratory fatigue, to detect environmental parameters that may be indicators of potential skin conditions, and/or to control environmental parameters under the face mask, among other examples. For example, as shown in FIG. 1A, the electronics module may include a microcontroller unit (MCU) with an integrated communication device (e.g., a Bluetooth or Bluetooth Low Energy transceiver), and various sensors that can sense or detect a condition or information associated with usage of the smart face mask. For example, as shown, the sensors included in the electronics module may include a gyroscope and/or a motion sensor (e.g., an accelerometer or inertial sensor) that can sense a six-axis position of the smart face mask, a breath sensor that can measure a respiratory rate or other respiration parameters (e.g., a breathing rhythm, inspiratory volume, or breathing effort), one or more temperature and/or humidity sensors to measure temperature and/or humidity outside the smart face mask and/or inside the smart face mask, and/or a sweat detection sensor that can measure a sweating rate and/or detect contents (e.g., analytes) in sweat, among other examples. Furthermore, as shown, the electronics module may include a power source (e.g., a rechargeable battery coupled to a direct current to direct current (DC-DC) charging driver circuit) to power the various other components of the electronics module. Alternatively, in some implementations, the electronics module may have no internal power source, and may instead using passive radio frequency identification (RFID) technology or energy harvesting to power the various other components of the electronics module (e.g., energy may be harvested from body motion of the wearer).

As described in further detail herein, the various sensors included in the electronics module may sense various conditions or information associated with usage of the smart face mask, a wearer of the smart face mask, and/or an environment of the smart face mask to enable real-time monitoring and/or tracking in a connected ecosystem. For example, as shown by reference number 104, the electronics module of the smart face mask may communicate with the user device via a wireless link (e.g., a wireless personal area network (WPAN), such as a Bluetooth network or piconet) to transmit real-time sensor data to the user device. The user device may then process different sets of measurements included in the real-time sensor data provided by the electronics module to determine the user mask wearing pattern, the user breathing pattern, and/or the user skin condition and provide alerts and/or recommendations related to the user mask wearing pattern, the user breathing pattern, and/or the user skin condition. Accordingly, as shown in FIG. 1A, and by reference number 106, the user device may provide one or more alerts or recommendations related to the user mask wearing pattern, the user breathing pattern, and/or the user skin condition, among other examples.

For example, in some implementations, the user device may process a set of measurements included in the sensor data that relate to a six-axis position of the face mask to determine whether the smart face mask is being worn in compliance with appropriate guidelines designed to reduce or mitigate a risk of the wearer spreading and/or contracting an airborne respiratory illness. For example, the guidelines may generally specify that a nose and a mouth of the wearer needs to be fully covered by a body of the smart face mask, and that the edges of the smart face mask should have a tight fit against the face of the wearer, to minimize inhalation or exhalation of pathogens or aerosolized contaminants. Accordingly, in some implementations, the user device may monitor the sensor data that relates to the position of the smart face mask to determine the user mask wearing pattern, which may indicate that the smart face mask was worn with both the mouth and nose properly covered, that the smart face mask only covered the mouth of the wearer, that the smart face mask only covered the nose of the wearer, that neither the mouth nor the nose were fully covered, that the smart face mask was pulled to one side or the other, and/or any other suitable mask wearing pattern. In some implementations, the user device may calibrate the smart face mask by obtaining a facial mapping of the user (e.g., using a facial recognition technology) that can be compared to the sensor data to determine whether the user's nose and/or mouth was covered while the user was wearing the smart face mask. In some implementations, in cases where the user device detects that the mask wearing pattern does not comply with applicable guidelines (e.g., the nose and/or mouth is uncovered), the user device may generate an alert or a recommendation to correct the position of the smart face mask.

Additionally, or alternatively, in some implementations, the user device may process a set of measurements included in the sensor data that relate to a user breathing pattern. For example, the user breathing pattern may be based on measurements that relate to a respiratory rate (e.g., a number of breaths per minute), a breathing rhythm, an inspiratory volume, or a breathing effort, which the user device may monitor to detect any breathing abnormalities that may be an indicator of a sickness or medical condition, or respiratory fatigue caused by usage of the smart face mask (e.g., users who have worn face masks for long periods have reported a need for occasional mask breaks to recover from respiratory fatigue). Furthermore, because normal and abnormal breathing patterns may vary for different activity levels, the sensor data provided by the electronics module may include measurements that indicate an activity state of the user (e.g., whether the user is sitting idle, walking, running, or sleeping). Accordingly, in some implementations, the user device may monitor the measurements in the sensor data that relate to the user breathing pattern to determine whether the user is at risk of a medical condition (e.g., a respiratory illness or ailment, such as asthma, chronic obstructive pulmonary disease (COPD), an infection such as influenza, pneumonia, tuberculosis, or COVID-19, or a lung disease such as lung cancer or emphysema). In some implementations, in cases where the user device detects an abnormal breathing pattern (e.g., shallow or rapid breaths) indicative of a medical condition or respiratory fatigue, the user device may generate an alert or a recommendation that the user remove the smart face mask in a well-ventilated area (e.g., outdoors) to obtain temporary relief and/or seek medical attention or treatment for a potential health issue. Furthermore, in cases where the smart face mask is equipped with a ventilator (e.g., a fan) and one or more actuation components to operate the ventilator (e.g., a brushless DC (BLDC) motor and driver), the user device may transmit a control command to the electronics module via the wireless link to turn the ventilator on (e.g., to pass some fresh air into the smart face mask to help improve the user breathing pattern), as shown by reference number 108.

Additionally, or alternatively, in some implementations, the user device may process a set of measurements included in the sensor data that relate to a skin condition of the user. For example, the sensor data may include measurements related to an external temperature outside the smart face mask, an internal temperature within the smart face mask, a humidity within the smart face mask, an on/off state of the ventilator (if present in the electronics module), moisture on the skin of the wearer of the smart face mask, and/or sweating data (e.g., a sodium or salt concentration), among other examples. Accordingly, the user device may process the measurements that relate to the skin condition of the user to determine whether the user is at risk of experiencing an adverse skin reaction caused by wearing the smart face mask (e.g., skin irritation behind the ears from wearing the smart face mask for a long time period, eczema or a rash caused by excessive moisture and/or heat, or other adverse skin reactions). In some implementations, in cases where the user device determines that the user is at risk of an adverse skin reaction, the user device may generate an alert or a recommendation that the user remove the smart face mask in a well-ventilated area to obtain temporary relief. Furthermore, in cases where the smart face mask is equipped with a ventilator, the user device may transmit a control command to the electronics module via the wireless link to turn the ventilator on (e.g., to reduce the temperature and/or humidity in the smart face mask), as shown by reference number 108.

As further shown by reference number 110, the user device may provide the face mask sensor data and/or information related to the user mask wearing pattern, the user breathing pattern, and/or the skin data analysis to a face mask analysis system (e.g., a server) that may perform more computationally intensive processing and/or use the data provided by the user device to enable face mask analytics across a wider user population. For example, as described in further detail below with reference to FIGS. 1B-1C, the user device may provide the face mask sensor data and/or information related to the user mask wearing pattern, the user breathing pattern, and/or the skin data analysis to a face mask analysis system in cases where the smart face mask is not connected to the user device or not in use (e.g., there is not a significant need for real-time monitoring, whereby the user may be able to tolerate the delay associated with the more computationally intensive processing performed by the face mask analytics system). Additionally, or alternatively, the face mask analytics system may use the data provided by the user device to derive patterns related to mask wearing behaviors associated with compliance or non-compliance with mask wearing guidelines, breathing patterns associated with respiratory illnesses or respiratory fatigue, and/or patterns in skin and/or environmental parameters that are associated with adverse skin reactions. In this way, the face mask analytics system may generate, obtain, and/or provide one or more data models that can be used to monitor user-specific mask wearing patterns, breathing patterns, and/or skin conditions.

In some implementations, in addition to generally enabling the user device to monitor a user mask wearing pattern, a user breathing pattern, and/or a user skin condition, the smart face mask may have applications in community, enterprise, healthcare, transit, or other settings where mask wearing is required or recommended. For example, in some implementations, the smart face mask may be equipped with an ultra-high-frequency (UHF) RFID tag configured to transmit a wireless beacon at periodic intervals, and gateways or other suitable devices may be deployed at various locations within a particular area to enable contact tracing within the area (e.g., a breakout area or cafeteria where a large number of people gather and there is an increased risk of transmitting respiratory illnesses due to people eating without their masks on). In this use case, the gateways or other devices may identify the wireless beacons that are transmitted by different smart face masks, and may store information related to the identities of the wireless beacons and the times and locations of the wireless beacons. In this way, when a case of a person with a respiratory illness is discovered or there is a cluster of cases, the information related to the identities, times, and locations of the wireless beacons may enable contact tracing to identify other people who were exposed and are at risk of contracting the respiratory illness. Furthermore, in environments where mask usage is required, an alert may be generated in cases where one or more users remove their face mask or their nose and/or mouth is uncovered to reduce the potential risk of spreading respiratory illnesses. In a similar respect, an alert may be generated when the sensor data indicates that one or more users are exhibiting breathing patterns that are indicative of a potential medical condition, so that those users may be sent home or otherwise removed from the area to prevent spreading illness to others.

Figure 1B:
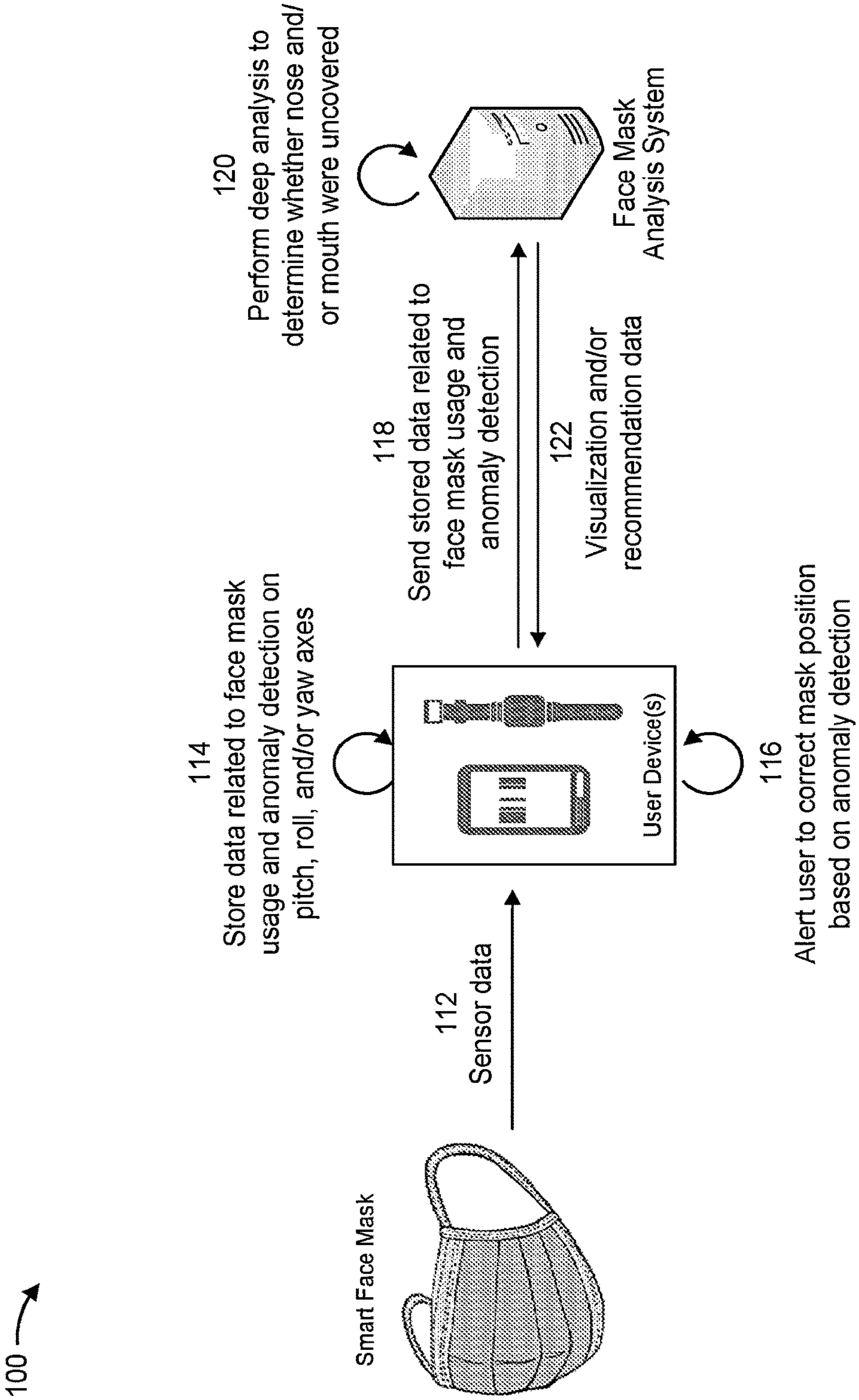

Referring now to FIG. 1B, the user device may be configured to determine a user mask wearing pattern in real-time based on sensor data provided by the electronics module of the smart face mask and/or may use the processing resources of the face mask analysis system to perform more computationally intensive analytics. For example, as described herein, the user device may determine the user mask wearing pattern in real-time in cases where the smart face mask is connected to the user device via a wireless link, or may invoke the processing resources of the face mask analysis system in cases where the smart face mask is not connected. For example, as shown by reference number 112, the user device may receive, acquire, or otherwise obtain six-axis gyroscope data from the electronics module of the smart face mask when the smart face mask is connected to the user device. The user device may then process the six-axis gyroscope data to determine whether the smart face mask is being used (e.g., is actively being worn on the user's face or sitting idle, such as on a desk), and may store data related to whether the mask is in use or not in use. As shown by reference number 114, the user device may further process the six-axis gyroscope data when the smart face mask is in use to determine the user mask wearing pattern (e.g., whether the smart face mask is covering the nose and mouth of the user) by performing edge anomaly detection on pitch, roll, and yaw axes. In some implementations, the user device may store the data related to the edge anomaly detection, which may indicate whether the smart face mask is being worn in compliance with appropriate masking guidelines and/or requirements. Furthermore, as shown by reference number 116, the user device may generate an alert to recommend that the user correct the positioning of the smart face mask in cases where one or more anomalies are detected from the gyroscope data.

Additionally, or alternatively, as shown by reference number 118, the user device may provide the stored data related to the mask wearing pattern and/or the anomaly detection performed locally on the user device to the face mask analytics system in cases where the smart face mask is not connected to the user device (e.g., using a wireless communication protocol). As shown by reference number 120, the face mask analytics system may then perform a deep analysis on the six-axis gyroscope data received from the electronics module of the smart face mask to determine the specific mask wearing pattern of the user. For example, the face mask analytics system may use one or more models that relate to typical mask wearing patterns, including patterns where the nose is uncovered, the mouth is uncovered, the nose and mouth are uncovered, the nose and mouth are both covered, or the like. Accordingly, the face mask analytics system may record information related to the user mask wearing pattern, and may return one or more data visualizations and/or recommendations to the user device, as shown by reference number 122. For example, in some implementations, the data visualizations may include an image or likeness of the user's face or a generic face, and may visually indicate how the smart face mask is currently being worn. In cases where the user needs to correct the positioning of the smart face mask, the data visualizations may further indicate the areas that need to be covered to be in compliance with the guidelines that relate to reducing the risk of the wearer spreading and/or contracting a respiratory illness. In some implementations, the user device may then generate one or more outputs to present the data visualizations and/or recommendations to the user.

Figure 1C:
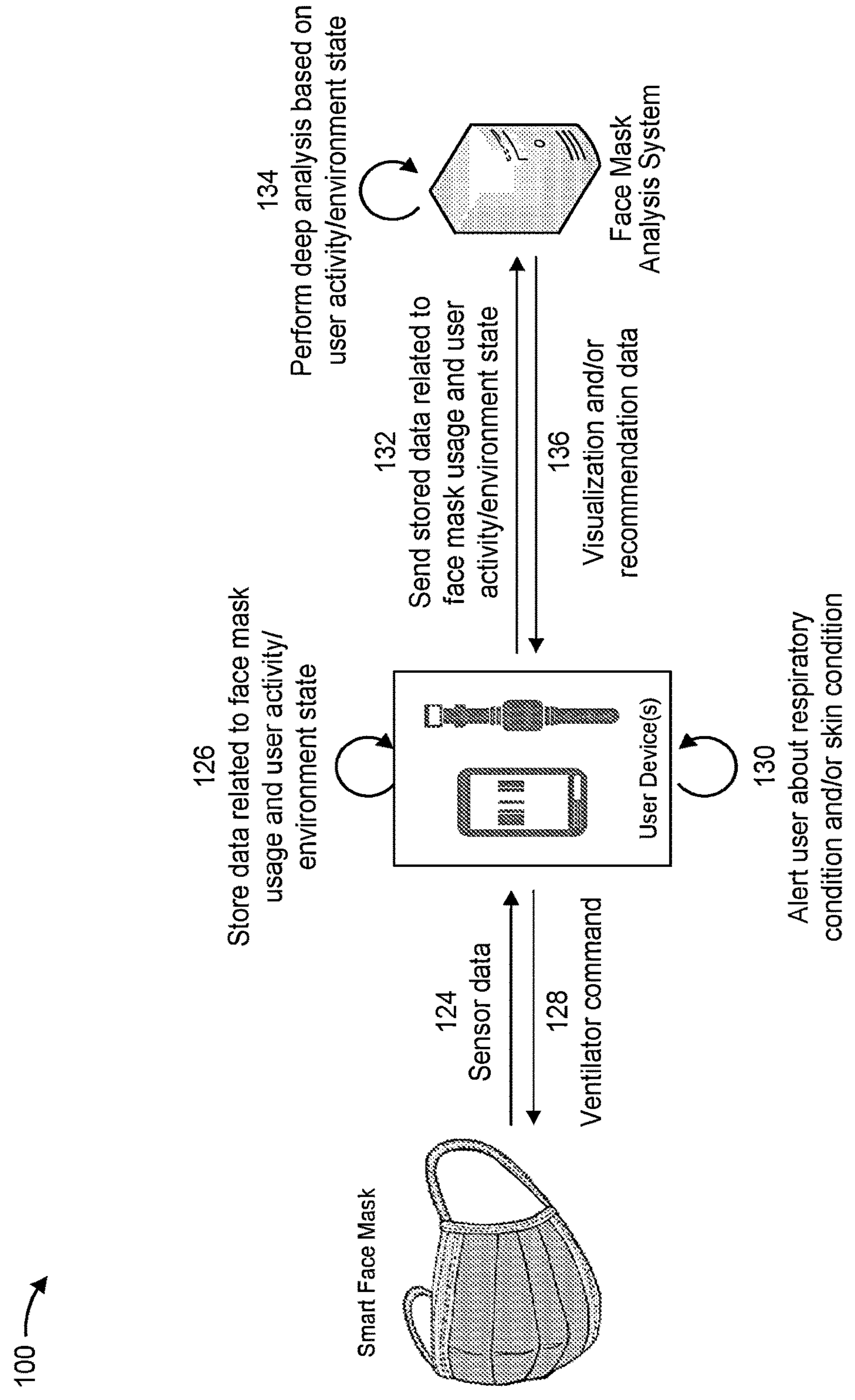

Referring now to FIG. 1C, the user device may be configured in a similar manner as described above to determine a user breathing pattern and/or perform a user skin analysis in real-time based on sensor data provided by the electronics module and/or may use the processing resources of the face mask analysis system to perform more computationally intensive analytics. For example, as described herein, the user device may determine the user breathing pattern and/or perform the skin analysis in real-time in cases where the smart face mask is connected to the user device via a wireless link, or may invoke the processing resources of the face mask analysis system in cases where the smart face mask is not connected. For example, as shown by reference number 124, the user device may receive, acquire, or otherwise obtain sensor data relevant to the user breathing pattern and/or skin analysis from the electronics module of the smart face mask when the smart face mask is connected to the user device. For example, in some implementations, the sensor data may include measurements from an air flow sensor, a skin moisture sensor, a temperature sensor, a humidity sensor, a breath sensor, an air quality indication (AQI) sensor, and/or six-axis gyroscope or motion data related to an activity state of the user. The user device may then process the sensor data to determine whether the smart face mask is being used, and may store data related to whether the mask is in use or not in use. As shown by reference number 126, the user device may further process the sensor data when the smart face mask is in use to determine the user breathing pattern by monitoring various measurements or parameters (e.g., whether the user's respiratory rate is significantly higher than normal or lower than normal for a given activity level, whether the user's inspiratory volume or breathing rhythm is consistent with a respiratory illness or other medical condition that may affect lung capacity or an ability to breathe effectively, or the like). Additionally, or alternatively, the user device may process the sensor data to determine whether the user is at risk of having an adverse skin reaction. Accordingly, in some implementations, the user device may store the data related to the user breathing pattern and/or the skin analysis (e.g., to enable further analytics and/or preserve a log of the user breathing pattern and/or the skin analysis). Furthermore, as shown by reference number 128, the user device may transmit a command to control a state of a ventilator included in the electronics module of the smart face mask (e.g., to turn the ventilator on or off) based on the user breathing pattern and/or the skin analysis. For example, the command may turn the ventilator on when the user breathing pattern indicates respiratory fatigue or a potential medical condition and/or when the skin analysis indicates that the user is at risk of an adverse skin reaction, or the command may turn the ventilator off (e.g., to save power) when the user breathing pattern indicates normal respiration and/or when the skin analysis indicates that the user does not have a significant risk of an adverse skin reaction. Furthermore, as shown by reference number 130, the user device may generate an alert to recommend that the user take a mask break or properly treat a potential medical condition that may be causing labored breathing or an adverse skin reaction.

Additionally, or alternatively, as shown by reference number 132, the user device may provide the stored data related to the user breathing pattern and/or the skin analysis performed locally on the user device to the face mask analytics system in cases where the smart face mask is not connected to the user device (e.g., using a wireless communication protocol). As shown by reference number 134, the face mask analytics system may then perform a deep analysis on the sensor data received from the electronics module of the smart face mask to determine the user breathing pattern and/or skin condition of the user. For example, the face mask analytics system may use one or more models that relate to normal user breathing patterns, breathing patterns that are consistent with respiration problems, respiratory fatigue, or other potential health issues, environmental parameters that are consistent with adverse skin reactions, mask wearing patterns that tend to lead to adverse skin reactions, or the like. For example, the face mask analytics system may perform the deep analysis of the user breathing pattern based on the various measurements that relate to respiration rates, breathing rhythms, or the like, where a normal or abnormal breathing pattern may vary depending on whether the user is walking, sitting, sleeping, running, or in another state of activity. Accordingly, the face mask analytics system may record information related to the user activity state and information that indicates whether the user is at risk of having a medical condition, at risk of experiencing respiratory fatigue, or at risk of experiencing an adverse skin reaction, and may return one or more data visualizations and/or recommendations based thereon to the user device, as shown by reference number 136. For example, in some implementations, the data visualizations may indicate the measurements that are indicative of a potential respiratory problem or skin condition and/or may include one or more recommendations (e.g., to take a mask break or properly treat a potential medical condition that may be causing an abnormal breathing pattern or adverse skin reaction).

Figure 1D:
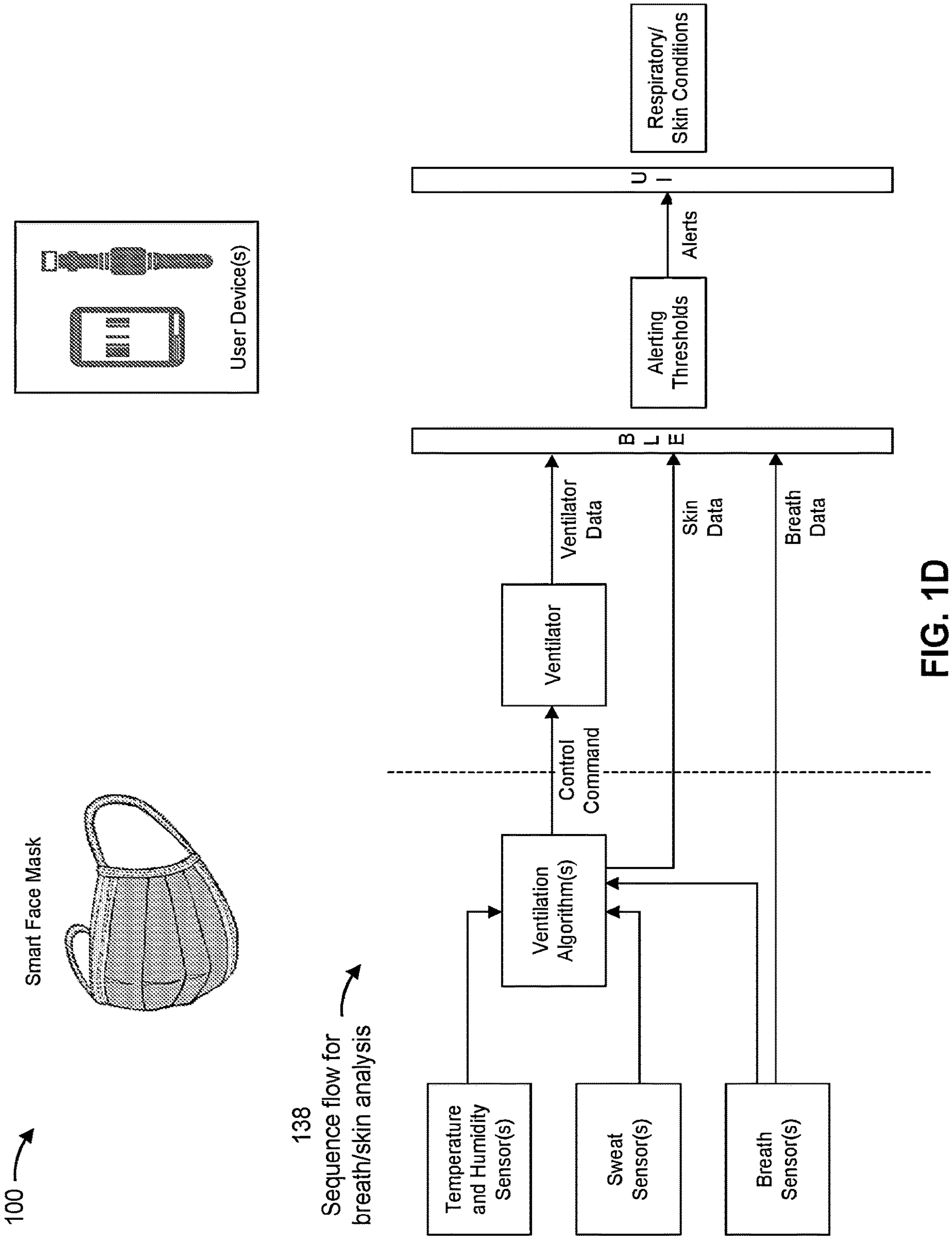

Referring now to FIG. 1D, reference number 138 illustrates an example sequence flow that includes various key events that are performed to generate the alerts and/or recommendations based on the user breathing pattern and/or skin analysis. For example, as shown, the electronics module of the smart face mask may support one or more ventilation algorithms (e.g., executed on or by the MCU) that receive input from various sensors, such as an external temperature sensor that provides a measurement of a temperature outside the smart face mask, an internal temperature sensor that provides a measurement of a temperature inside the smart face mask, an internal humidity sensor that provides a measurement of a humidity inside the smart face mask, a sweat sensor that provides a measurement related to a sweating rate or sweat contents taken from moisture on the skin of the user, and/or a breath sensor that provides a measurement related to a number of breaths, an inspiratory volume, or the like. Accordingly, the ventilation algorithm(s) may be configured to detect one or more conditions based on the sensor data, which may be used as inputs to determine whether to turn the ventilator (fan) on or off. For example, a rise in temperature, a rise in skin humidity, a high sweating rate, and/or an abnormal breathing pattern may be indicators to turn the ventilator on, whereas a decrease in temperature, a decrease in skin humidity, a low sweating rate, and/or a normal breathing pattern may be indicators to turn the ventilator off. In some implementations, the sensor data may therefore be used to generate one or more indicators of whether to turn the ventilator on or off, which the ventilation algorithm(s) may use to generate an appropriate command to control the ventilator.

As further shown in FIG. 1D, the sensor data related to the skin condition of the user and the breathing pattern of the user may be provided to the user device via a wireless link (shown as a Bluetooth Low Energy (BLE) link) along with information indicating whether the ventilator is on or off. In the illustrated example, the user device may then map the sensor data and the ventilator data to the user breathing pattern and/or skin condition of the user based on one or more alerting thresholds. For example, the one or more alerting thresholds may be used to generate an alert, a recommendation, or a command to turn the ventilator on if the ventilator has been off for a threshold time period (e.g., more than thirty minutes) and the amount of time that the user has been wearing the smart face mask satisfies a threshold (e.g., to prevent suffocation or an oxygen deficiency). In other examples, an alert, recommendation, or ventilator command may be generated when a sweating condition satisfies a threshold to prevent a skin condition such as acne or irritated skin, when a skin humidity satisfies a threshold and the mask wearing time satisfies a threshold to prevent eczema or an allergic skin reaction, when the skin humidity satisfies a threshold and a skin temperature satisfies a threshold to prevent a skin breakout, and/or when the mask wearing time satisfies a threshold to prevent suffocation, oxygen deficiency, and/or sore skin behind the ears, among other examples.

As indicated above, FIGS. 1A-1D are provided as an example. Other examples may differ from what is described with regard to FIGS. 1A-1D. The number and arrangement of devices shown in FIGS. 1A-1D are provided as an example. In practice, there may be additional devices, fewer devices, different devices, or differently arranged devices than those shown in FIGS. 1A-1D. Furthermore, two or more devices shown in FIGS. 1A-1D may be implemented within a single device, or a single device shown in FIGS. 1A-1D may be implemented as multiple, distributed devices. Additionally, or alternatively, a set of devices (e.g., one or more devices) shown in FIGS. 1A-1D may perform one or more functions described as being performed by another set of devices shown in FIGS. 1A-1D.

Figure 2A:
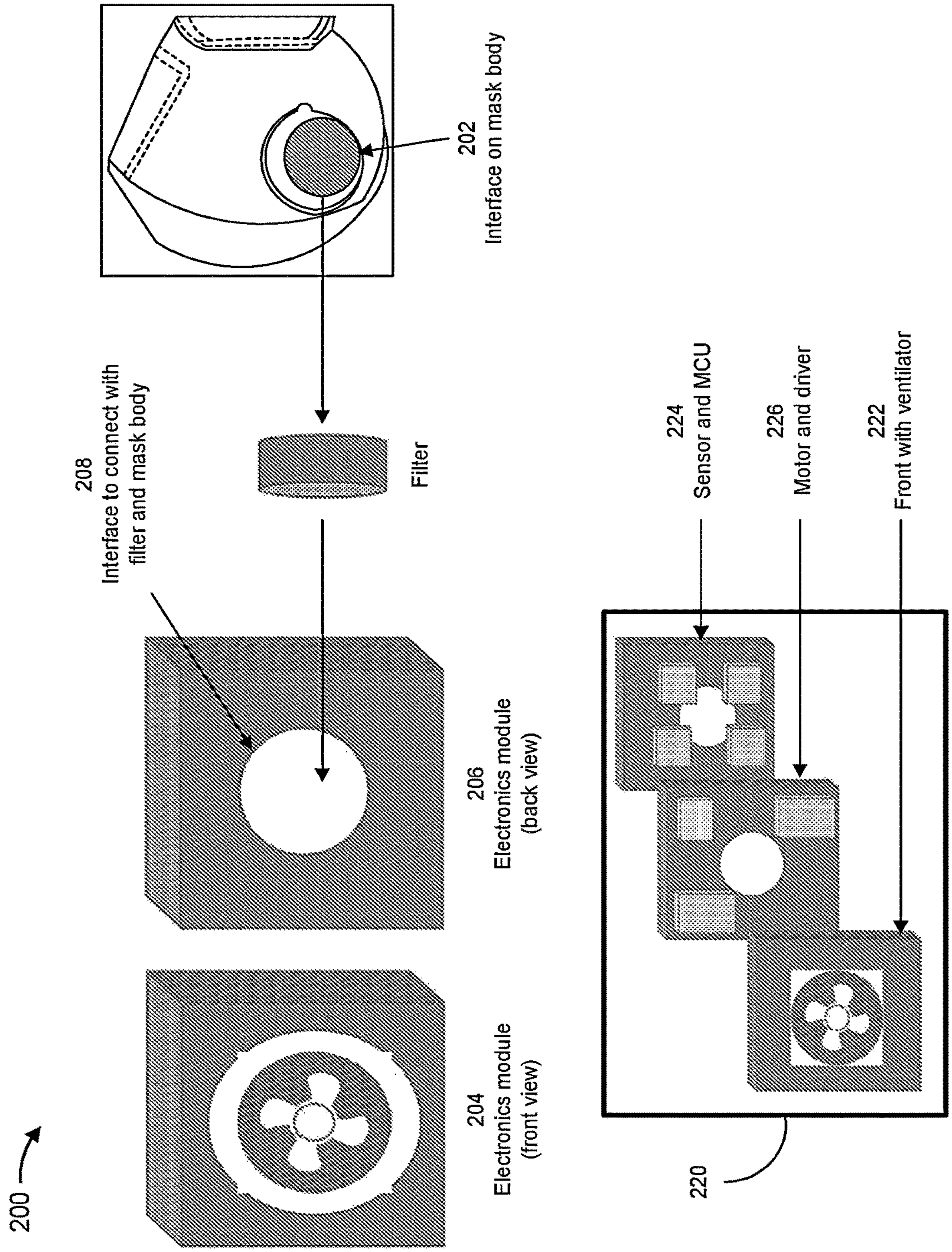
FIGS. 2A-2C are diagrams of one or more example implementations associated with a connected smart face mask with intelligent tracking.
Figure 2B:
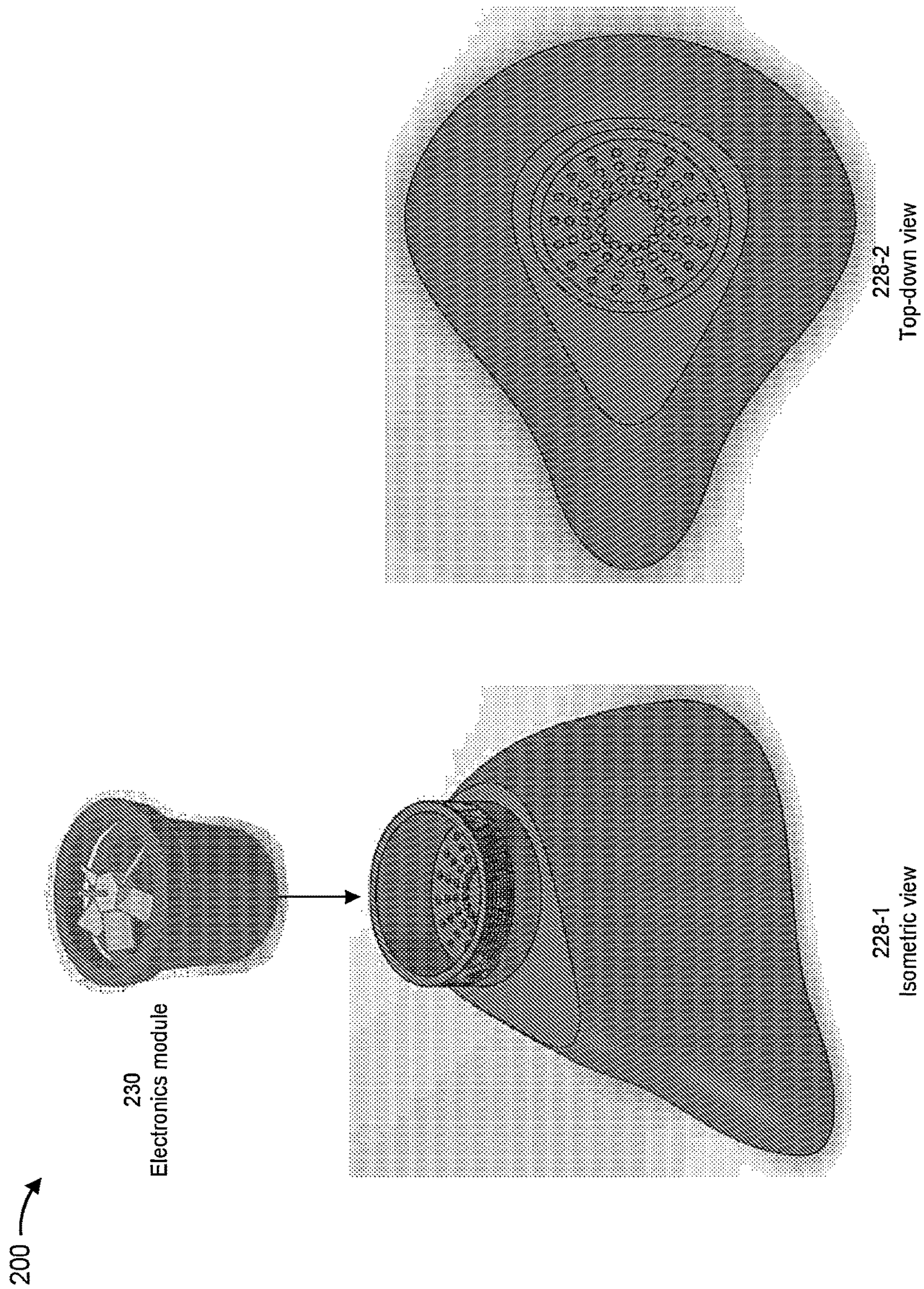
Figure 2C:
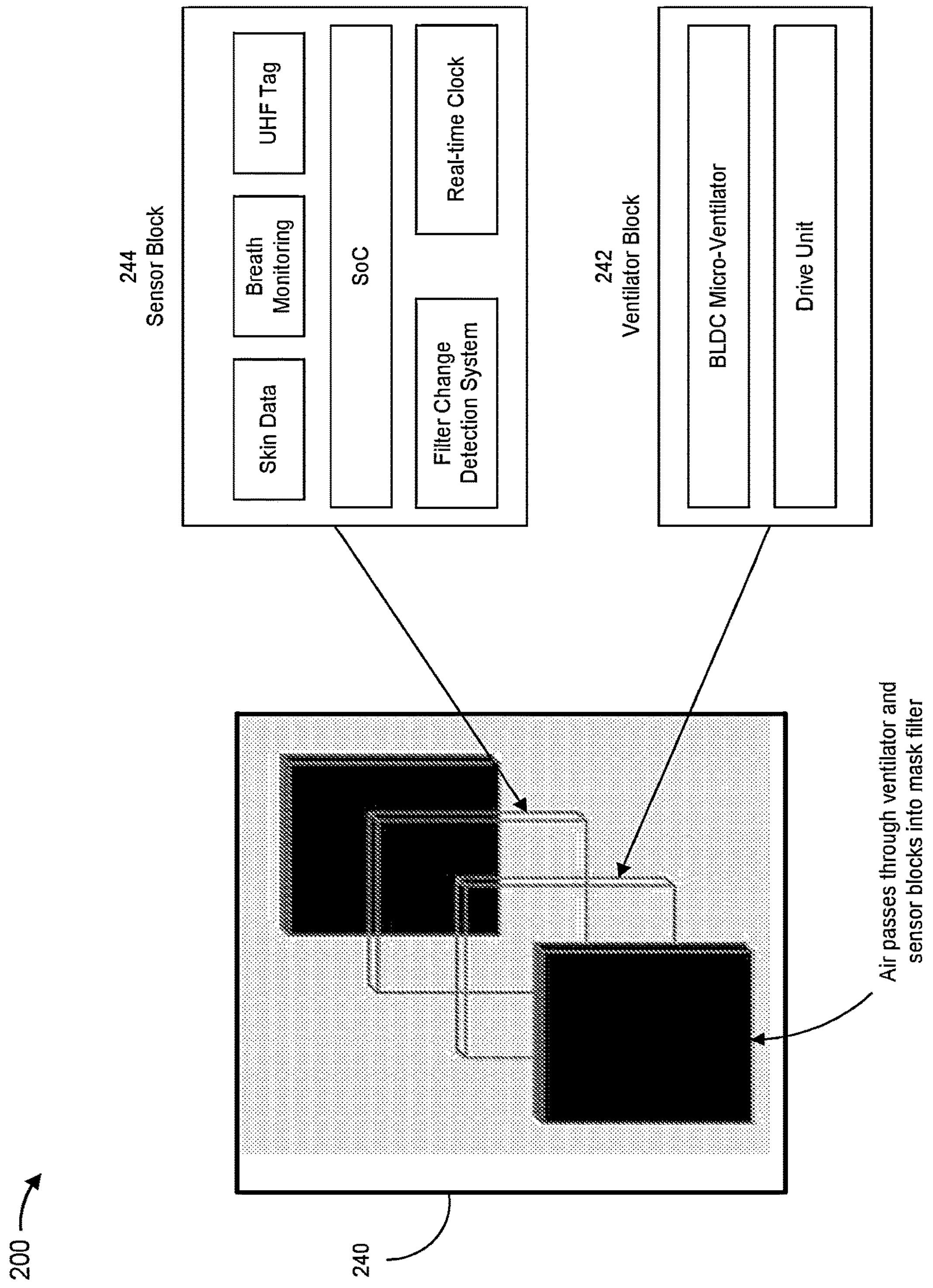

FIGS. 2A-2C are diagrams of one or more example implementations 200 associated with a connected smart face mask with intelligent tracking. As shown in FIGS. 2A-2C, example implementations 200 illustrate structural designs that may be used for the smart face mask described above with reference to FIGS. 1A-1D.

For example, referring to FIG. 2A, reference number 202 depicts an example design for the smart face mask, which includes a mask body and an interface (e.g., a grooved region) for receiving an electronics module and a removable filter (e.g., a high-efficiency particulate air (HEPA) filter, a medical grade particulate filter, or the like). For example, reference number 204 illustrates a front view of the electronics module and reference number 206 illustrates a back view of the electronics module, where an interface is provided on the back of the electronics module to connect with the filter and the mask body. As shown in FIG. 2A, and by reference number 220, the electronics module may have a layered structure, which may include a front (e.g., outward-facing) layer 222 that includes the ventilator, a back (e.g., user-facing) layer 224 that includes various sensors, an MCU, and the interface for receiving the filter, and a middle layer 226 that includes a BLDC motor and driver for controlling the ventilator (e.g., the driver may receive control commands from the MCU and may operate the BLDC motor to turn the ventilator on or off based on the control commands received from the MCU).

FIG. 2B illustrates example three-dimensional views of the connected smart face mask. For example, FIG. 2B illustrates an isometric view 228-1 of the connected smart face mask and a top-down view 228-2 of the connected smart face mask, which includes a mask body capable of covering a user's respiratory orifices (e.g., nose and mouth) and an interface to receive the electronics module 230. For example, as shown, the interface may have a shape (e.g., a circular shape in the illustrated example) that is mated to a shape of the electronics module to ensure a tight fit and securely fix all electronic components.

Referring to FIG. 2C, reference number 240 illustrates another example layered structure of the electronics module, which includes a front (e.g., outward-facing) layer where air passes through the front layer, through a ventilator block 242, and through a sensor block 244 before passing through the mask filter. As shown, the ventilator block 242 may include a BLDC micro-ventilator and a drive unit for controlling the BLDC micro-ventilator, and the sensor block 244 may include one or more skin data sensors, one or more breath monitoring sensors, a UHF tag that may transmit wireless beacons at periodic intervals, a system-on-chip (e.g., an MCU), a real-time clock, and a filter change detection system (e.g., to indicate when the filter needs to be changed and/or detect when the filter is changed).

Accordingly, as described herein, the connected smart face mask may have a modular design with various replaceable components (e.g., the filter, the electronics module, the ventilator, or the like), and may consume a very small amount of power. For example, the MCU or system-on-chip may use Bluetooth Low Energy (BLE) to communicate over a wireless link, and may offer a battery backup that can last two to three weeks after a single charge cycle. Furthermore, in some implementations, the MCU or system-on-chip may include a feature to transition to a deep sleep mode to save power when the smart face mask is not in use. Additionally, or alternatively, rather than having an internal power source, the electronics module may use passive RFID technology or energy harvesting to power the various components of the electronics module (e.g., by harvesting energy from body motion of the wearer). In addition, the connected smart face mask may communicate with a user device or other external devices to enable viewing data dashboards that include information related to the user mask wearing pattern, user breathing pattern, or user skin condition over time.

As indicated above, FIGS. 2A-2C are provided as an example. Other examples may differ from what is described with regard to FIGS. 2A-2C. The number and arrangement of devices shown in FIGS. 2A-2C are provided as an example. In practice, there may be additional devices, fewer devices, different devices, or differently arranged devices than those shown in FIGS. 2A-2C. Furthermore, two or more devices shown in FIGS. 2A-2C may be implemented within a single device, or a single device shown in FIGS. 2A-2C may be implemented as multiple, distributed devices. Additionally, or alternatively, a set of devices (e.g., one or more devices) shown in FIGS. 2A-2C may perform one or more functions described as being performed by another set of devices shown in FIGS. 2A-2C.

Figure 3:
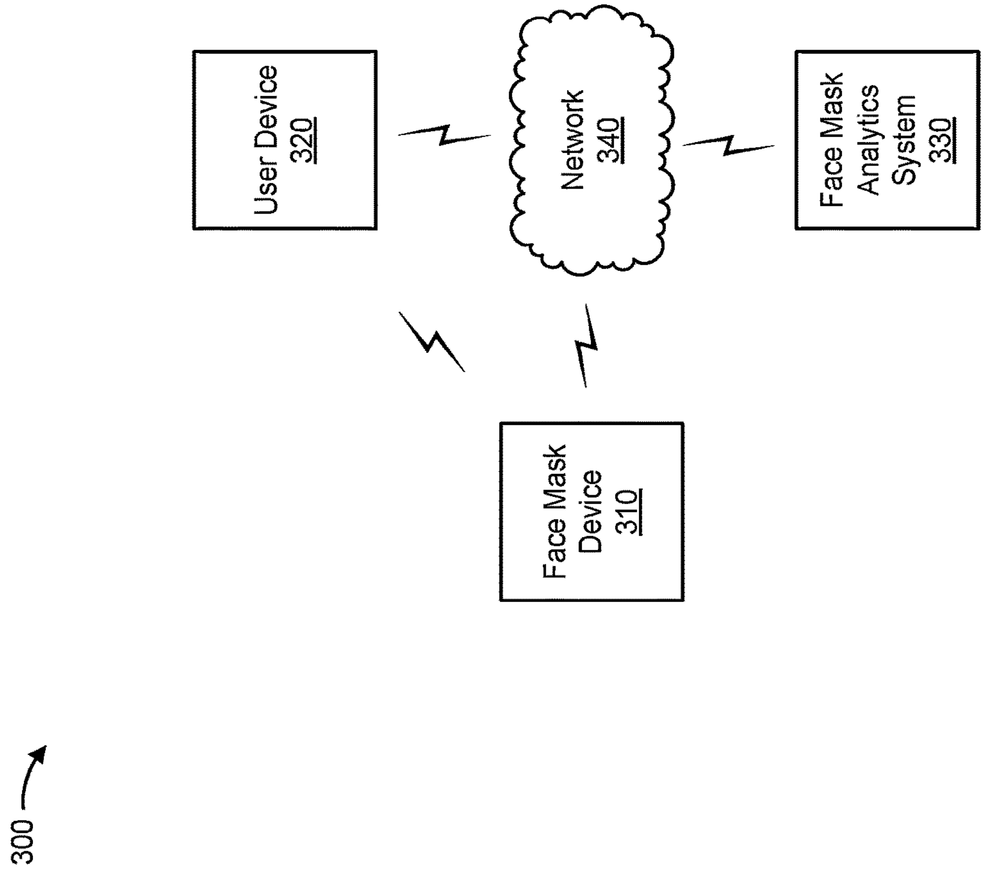
FIG. 3 is a diagram of an example environment in which systems and/or methods described herein may be implemented.

FIG. 3 is a diagram of an example environment 300 in which systems and/or methods described herein may be implemented. As shown in FIG. 3, environment 300 may include a face mask device 310, a user device 320, a face mask analytics system 330, and a network 340. Devices of environment 300 may interconnect via wired connections, wireless connections, or a combination of wired and wireless connections.

The face mask device 310 includes a mask body capable of covering a user's respiratory orifices (e.g., nose and mouth) and an electronics module capable of receiving, generating, storing, processing, and/or providing information associated with a user mask wearing pattern, a user breathing pattern, or a user skin condition, as described elsewhere herein. For example, in some implementations, the face mask device 310 may have a structure and/or design as shown in FIGS. 2A-2C and described in further detail above.

The user device 320 includes one or more devices capable of receiving, generating, storing, processing, and/or providing information associated with a connected smart face mask with intelligent tracking, as described elsewhere herein. The user device 320 may include a communication device and/or a computing device. For example, the user device 320 may include a wireless communication device, a mobile phone, a user equipment, a laptop computer, a tablet computer, a desktop computer, a gaming console, a set-top box, a wearable communication device (e.g., a smart wristwatch, a pair of smart eyeglasses, a head mounted display, or a virtual reality headset), a human-machine interface or infotainment system in a vehicle, or a similar type of device.

The face mask analytics system 330 includes one or more devices capable of receiving, generating, storing, processing, providing, and/or routing information associated with a connected smart face mask with intelligent tracking, as described elsewhere herein. The face mask analytics system 330 may include a communication device and/or a computing device. For example, the face mask analytics system 330 may include a server, such as an application server, a client server, a web server, a database server, a host server, a proxy server, a virtual server (e.g., executing on computing hardware), or a server in a cloud computing system. In some implementations, the face mask analytics system 330 includes computing hardware used in a cloud computing environment.

The network 340 includes one or more wired and/or wireless networks. For example, the network 340 may include a wireless wide area network (e.g., a cellular network or a public land mobile network), a local area network (e.g., a wired local area network or a wireless local area network (WLAN), such as a Wi-Fi network), a personal area network (e.g., a Bluetooth network), a near-field communication network, a telephone network, a private network, the Internet, and/or a combination of these or other types of networks. The network 340 enables communication among the devices of environment 300.

The number and arrangement of devices and networks shown in FIG. 3 are provided as an example. In practice, there may be additional devices and/or networks, fewer devices and/or networks, different devices and/or networks, or differently arranged devices and/or networks than those shown in FIG. 3. Furthermore, two or more devices shown in FIG. 3 may be implemented within a single device, or a single device shown in FIG. 3 may be implemented as multiple, distributed devices. Additionally, or alternatively, a set of devices (e.g., one or more devices) of environment 300 may perform one or more functions described as being performed by another set of devices of environment 300.

Figure 4:
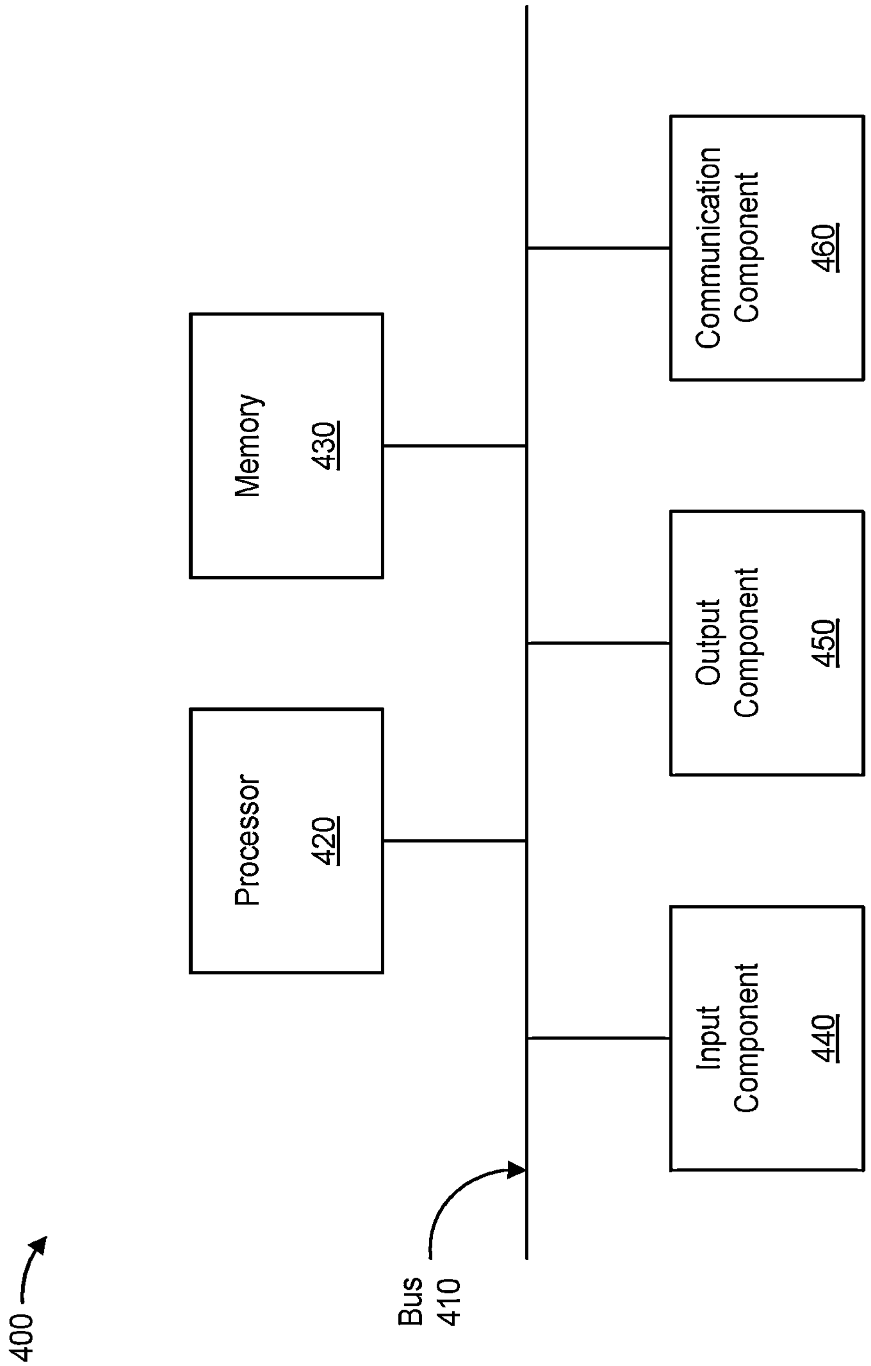
FIG. 4 is a diagram of example components of one or more devices of FIG. 3.

FIG. 4 is a diagram of example components of a device 400, which may correspond to face mask device 310, user device 320, and/or face mask analytics system 330. In some implementations, face mask device 310, user device 320, and/or face mask analytics system 330 include one or more devices 400 and/or one or more components of device 400. As shown in FIG. 4, device 400 may include a bus 410, a processor 420, a memory 430, an input component 440, an output component 450, and a communication component 460.

Bus 410 includes one or more components that enable wired and/or wireless communication among the components of device 400. Bus 410 may couple together two or more components of FIG. 4, such as via operative coupling, communicative coupling, electronic coupling, and/or electric coupling. Processor 420 includes a central processing unit, a graphics processing unit, a microprocessor, a controller, a microcontroller, a digital signal processor, a field-programmable gate array, an application-specific integrated circuit, and/or another type of processing component. Processor 420 is implemented in hardware, firmware, or a combination of hardware and software. In some implementations, processor 420 includes one or more processors capable of being programmed to perform one or more operations or processes described elsewhere herein.

Memory 430 includes volatile and/or nonvolatile memory. For example, memory 430 may include random access memory (RAM), read only memory (ROM), a hard disk drive, and/or another type of memory (e.g., a flash memory, a magnetic memory, and/or an optical memory). Memory 430 may include internal memory (e.g., RAM, ROM, or a hard disk drive) and/or removable memory (e.g., removable via a universal serial bus connection). Memory 430 may be a non-transitory computer-readable medium. Memory 430 stores information, instructions, and/or software (e.g., one or more software applications) related to the operation of device 400. In some implementations, memory 430 includes one or more memories that are coupled to one or more processors (e.g., processor 420), such as via bus 410.

Input component 440 enables device 400 to receive input, such as user input and/or sensed input. For example, input component 440 may include a touch screen, a keyboard, a keypad, a mouse, a button, a microphone, a switch, a sensor, a global positioning system sensor, an accelerometer, a gyroscope, and/or an actuator. Output component 450 enables device 400 to provide output, such as via a display, a speaker, and/or a light-emitting diode. Communication component 460 enables device 400 to communicate with other devices via a wired connection and/or a wireless connection. For example, communication component 460 may include a receiver, a transmitter, a transceiver, a modem, a network interface card, and/or an antenna.

Device 400 may perform one or more operations or processes described herein. For example, a non-transitory computer-readable medium (e.g., memory 430) may store a set of instructions (e.g., one or more instructions or code) for execution by processor 420. Processor 420 may execute the set of instructions to perform one or more operations or processes described herein. In some implementations, execution of the set of instructions, by one or more processors 420, causes the one or more processors 420 and/or the device 400 to perform one or more operations or processes described herein. In some implementations, hardwired circuitry is used instead of or in combination with the instructions to perform one or more operations or processes described herein. Additionally, or alternatively, processor 420 may be configured to perform one or more operations or processes described herein. Thus, implementations described herein are not limited to any specific combination of hardware circuitry and software.

The number and arrangement of components shown in FIG. 4 are provided as an example. Device 400 may include additional components, fewer components, different components, or differently arranged components than those shown in FIG. 4. Additionally, or alternatively, a set of components (e.g., one or more components) of device 400 may perform one or more functions described as being performed by another set of components of device 400.

Figure 5:
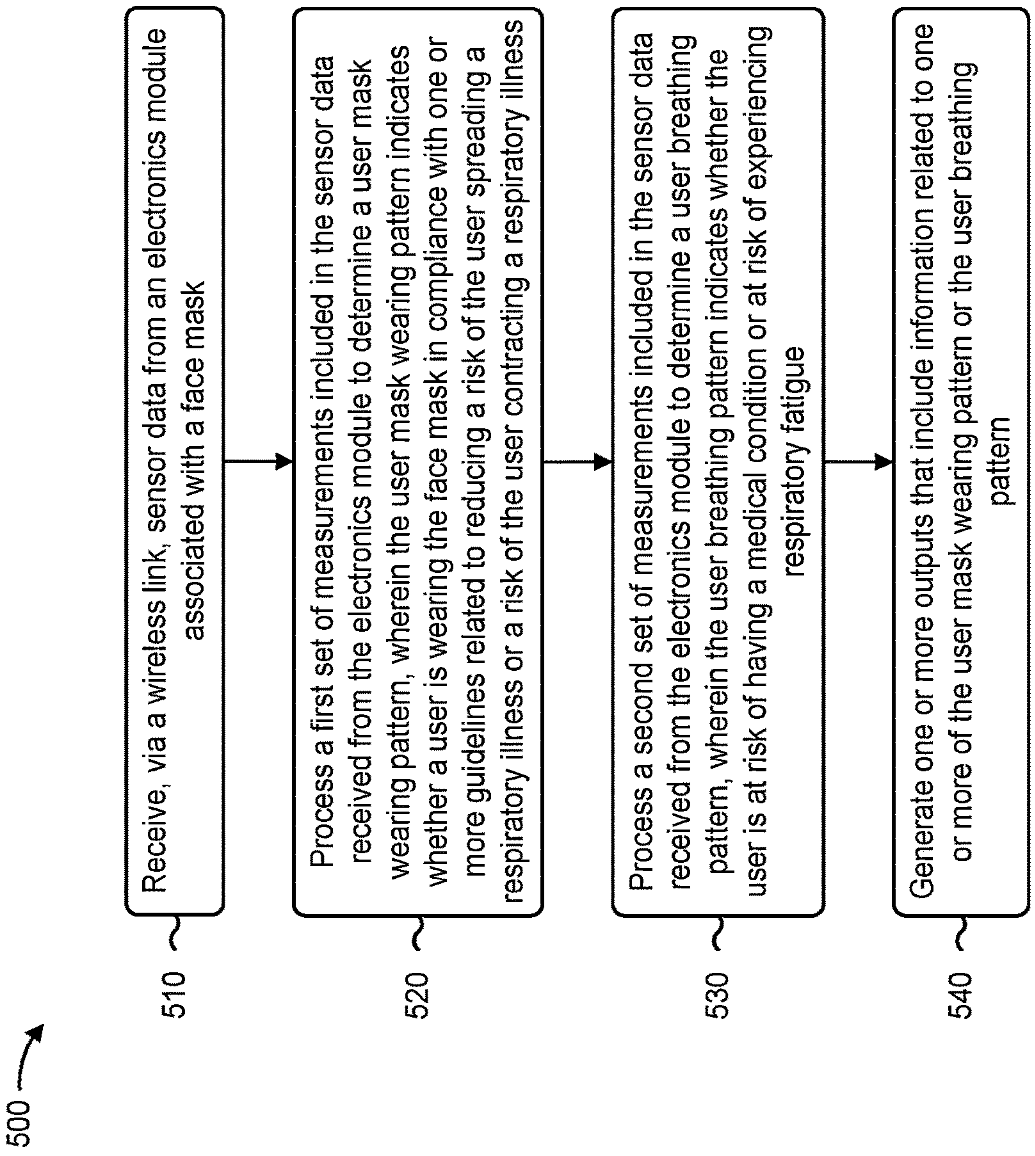
FIG. 5 is a flowchart of an example process associated with a connected smart face mask with intelligent tracking.

FIG. 5 is a flowchart of an example process 500 associated with a connected smart face mask with intelligent tracking. In some implementations, one or more process blocks of FIG. 5 are performed by a user device (e.g., user device 320). In some implementations, one or more process blocks of FIG. 5 are performed by another device or a group of devices separate from or including the user device, such as a face mask device (e.g., face mask device 310) and/or a face mask analytics system (e.g., face mask analytics system 330). Additionally, or alternatively, one or more process blocks of FIG. 5 may be performed by one or more components of device 400, such as processor 420, memory 430, input component 440, output component 450, and/or communication component 460.

As shown in FIG. 5, process 500 may include receiving sensor data from an electronics module associated with a face mask (block 510). For example, the user device may receive sensor data from an electronics module associated with a face mask, as described above.

As further shown in FIG. 5, process 500 may include processing a first set of measurements included in the sensor data received from the electronics module to determine a user mask wearing pattern, wherein the user mask wearing pattern indicates whether a user is wearing the face mask in compliance with one or more guidelines related to reducing a risk of the user spreading a respiratory illness or a risk of the user contracting a respiratory illness (block 520). For example, the user device may process a first set of measurements included in the sensor data received from the electronics module to determine a user mask wearing pattern, wherein the user mask wearing pattern indicates whether a user is wearing the face mask in compliance with one or more guidelines related to reducing a risk of the user spreading a respiratory illness or a risk of the user contracting a respiratory illness, as described above. In some implementations, the user mask wearing pattern indicates whether a user is wearing the face mask in compliance with one or more guidelines related to reducing a risk of the user spreading a respiratory illness or a risk of the user contracting a respiratory illness.

As further shown in FIG. 5, process 500 may include processing a second set of measurements included in the sensor data received from the electronics module to determine a user breathing pattern, wherein the user breathing pattern indicates whether the user is at risk of having a medical condition or at risk of experiencing respiratory fatigue (block 530). For example, the user device may process a second set of measurements included in the sensor data received from the electronics module to determine a user breathing pattern, wherein the user breathing pattern indicates whether the user is at risk of having a medical condition or at risk of experiencing respiratory fatigue, as described above. In some implementations, the user breathing pattern indicates whether the user is at risk of having a medical condition or at risk of experiencing respiratory fatigue.

As further shown in FIG. 5, process 500 may include generating one or more outputs that include information related to one or more of the user mask wearing pattern or the user breathing pattern (block 540). For example, the user device may generate one or more outputs that include information related to one or more of the user mask wearing pattern or the user breathing pattern, as described above.

Process 500 may include additional implementations, such as any single implementation or any combination of implementations described below and/or in connection with one or more other processes described elsewhere herein.

In a first implementation, the first set of measurements that are processed to determine the user mask wearing pattern relate to a six-axis position of the face mask relative to a nose of the user and a mouth of the user.

In a second implementation, alone or in combination with the first implementation, the one or more outputs include an alert or a recommendation to adjust a positioning of the face mask based on the user mask wearing pattern indicating that one or more of a nose of the user or a mouth of the user is uncovered.

In a third implementation, alone or in combination with one or more of the first and second implementations, the second set of measurements that are processed to determine the user breathing pattern relate to one or more of a respiratory rate, a breathing rhythm, an inspiratory volume, or a breathing effort of the user.

In a fourth implementation, alone or in combination with one or more of the first through third implementations, the second set of measurements that are processed to determine the breathing pattern of the user further relate to a state of activity of the user.

In a fifth implementation, alone or in combination with one or more of the first through fourth implementations, process 500 includes transmitting, to the electronics module via the wireless link, a command to control a state of a ventilator included in the electronics module based on the user breathing pattern.

In a sixth implementation, alone or in combination with one or more of the first through fifth implementations, process 500 includes processing a third set of measurements included in the sensor data received from the electronics module to determine a user skin condition, wherein the user skin condition indicates whether the user is at risk of experiencing an adverse skin reaction caused by wearing the face mask.

In a seventh implementation, alone or in combination with one or more of the first through sixth implementations, the third set of measurements that are processed to determine the user skin condition relate to one or more of an external temperature outside the face mask, an internal temperature under the face mask, an internal humidity under the face mask, a sweating state of the user, or a state of a ventilator included in the electronics module.

In an eighth implementation, alone or in combination with one or more of the first through seventh implementations, process 500 includes transmitting, to the electronics module via the wireless link, a command to control a state of a ventilator included in the electronics module based on the user skin condition.

In a ninth implementation, alone or in combination with one or more of the first through eighth implementations, process 500 includes transmitting, to a server, at least a portion of the sensor data received from the electronics module associated with the face mask or data related to the user mask wearing pattern, the user breathing pattern, or a user skin condition, and receiving, from the server, face mask analytics data based on the sensor data or the data related to the user mask wearing pattern, the user breathing pattern, or the user skin condition.

Although FIG. 5 shows example blocks of process 500, in some implementations, process 500 includes additional blocks, fewer blocks, different blocks, or differently arranged blocks than those depicted in FIG. 5. Additionally, or alternatively, two or more of the blocks of process 500 may be performed in parallel.

The foregoing disclosure provides illustration and description, but is not intended to be exhaustive or to limit the implementations to the precise forms disclosed. Modifications may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, not equal to the threshold, or the like.

Although particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, or a combination of related and unrelated items), and may be used interchangeably with "one or more." Where only one item is intended, the phrase "only one" or similar language is used.

Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:

receiving, by a user device via a wireless link, sensor data from an electronics module integrated into a face mask, the electronics module including one or more sensors and a microcontroller;

processing, by the user device, a first set of measurements included in the sensor data received from the electronics module to determine a user mask wearing pattern, wherein the user mask wearing pattern indicates whether a user is wearing the face mask in compliance with one or more guidelines related to reducing a risk of the user spreading a respiratory illness or a risk of the user contracting a respiratory illness;

processing, by the user device, a second set of measurements included in the sensor data received from the electronics module to determine a user breathing pattern, wherein the user breathing pattern indicates whether the user is at risk of having a medical condition or at risk of experiencing respiratory fatigue; and generating, by the user device, one or more outputs that include information related to one or more of the user mask wearing pattern or the user breathing pattern, wherein the first set of measurements that are processed to determine the user mask wearing pattern relate to a six-axis position of the face mask relative to a nose of the user and a mouth of the user.

2. The method of claim 1, wherein the one or more outputs include an alert or a recommendation to adjust a positioning of the face mask based on the user mask wearing pattern indicating that one or more of a nose of the user or a mouth of the user is uncovered.

3. The method of claim 1, further comprising:

transmitting, to the electronics module via the wireless link, a command to control a state of a fan included in the electronics module based on the user breathing pattern.

4. The method of claim 1, further comprising:

transmitting, to a server, at least a portion of the sensor data received from the electronics module associated with the face mask or data related to the user mask wearing pattern, the user breathing pattern, or a user skin condition; and receiving, from the server, face mask analytics data based on the sensor data or the data related to the user mask wearing pattern, the user breathing pattern, or the user skin condition.

5. The method of claim 1, wherein the second set of measurements that are processed to determine the user breathing pattern relate to one or more of a respiratory rate, a breathing rhythm, an inspiratory volume, or a breathing effort of the user.

6. The method of claim 5, wherein the second set of measurements that are processed to determine the breathing pattern of the user further relate to a state of activity of the user.

7. The method of claim 1, further comprising:

processing a third set of measurements included in the sensor data received from the electronics module to determine a user skin condition, wherein the user skin condition indicates whether the user is at risk of experiencing an adverse skin reaction caused by wearing the face mask.

8. The method of claim 7, wherein the third set of measurements that are processed to determine the user skin condition relate to one or more of an external temperature outside the face mask, an internal temperature under the face mask, an internal humidity under the face mask, a sweating state of the user, or a state of a fan included in the electronics module.

9. The method of claim 7, further comprising:

transmitting, to the electronics module via the wireless link, a command to control a state of a fan included in the electronics module based on the user skin condition.

* * * * *